United States Patent [19]

Ferrell

[11] Patent Number: 4,670,131
[45] Date of Patent: Jun. 2, 1987

[54] METHOD FOR CONTROLLING FOULING OF HYDROCARBON COMPOSITIONS CONTAINING OLEFINIC COMPOUNDS

[75] Inventor: Thomas M. Ferrell, Houston, Tex.

[73] Assignee: Exxon Chemical Patents Inc., Linden, N.J.

[21] Appl. No.: 818,583

[22] Filed: Jan. 13, 1986

[51] Int. Cl.$^4$ .................... C10G 9/12; C10G 9/16
[52] U.S. Cl. .................... 208/48 AA; 203/9; 585/950; 208/348; 252/8.3
[58] Field of Search .................... 208/48 AA, 348; 585/952, 950; 203/8, 9; 252/8.3, 405–407

[56] References Cited

U.S. PATENT DOCUMENTS

| | | | |
|---|---|---|---|
| 2,900,421 | 8/1959 | Kharasch et al. | 203/9 |
| 3,408,266 | 10/1968 | Ward | 203/9 |
| 3,494,930 | 2/1970 | Duheyre et al. | 546/183 |
| 3,551,507 | 12/1970 | Sakuragi et al. | 208/48 AA |
| 3,704,233 | 11/1972 | Eich et al. | 546/67 |
| 3,733,326 | 5/1973 | Murayama et al. | 546/187 |
| 3,747,988 | 7/1973 | Bailey | 203/8 |
| 3,966,711 | 6/1976 | Rasberger | 260/239.3 R |
| 4,000,201 | 12/1976 | Weinshenker | 252/406 |
| 4,002,554 | 1/1977 | Borge et al. | 208/48 AA |
| 4,009,094 | 2/1977 | Cole et al. | 208/48 AA |
| 4,158,027 | 6/1979 | Restaino | 208/48 AA |
| 4,191,614 | 3/1980 | Watson et al. | 203/9 |
| 4,237,326 | 12/1980 | Fuga et al. | 585/952 |

Primary Examiner—Andrew H. Metz
Assistant Examiner—Anthony McFarlane
Attorney, Agent, or Firm—R. L. Graham

[57] ABSTRACT

Fouling of equipment used for processing of organic feed streams containing olefinic compounds is controlled by inhibiting polymerization of the olefinic compounds by carrying out the processing in the presence of from about 20 ppb to less than 1000 ppb of a stable free radical, such as a nitroxide.

20 Claims, 1 Drawing Figure

METHOD FOR CONTROLLING FOULING OF HYDROCARBON COMPOSITIONS CONTAINING OLEFINIC COMPOUNDS

BACKGROUND OF THE INVENTION

1. Field of the Invention

The present invention relates to a method for controlling fouling in equipment for processing and storing hydrocarbon compositions containing unsaturated compounds. More specifically the processing may include, for example, preheating, hydrogenation, fractionation, extraction and the like of hydrocarbon streams to remove, concentrate, or have added thereto the unsaturated hydrocarbons prior to storage or use.

The process of recovering olefinic hydrocarbons from gas and liquid cracking operations, the conversion of olefinic and acetylenic compounds by, for example hydrogenation and the separation of the various olefins and acetylenic compounds by distillation or extraction is complicated by the formation of fouling deposits on the heat transfer surfaces of the processing equipment. These deposits decrease the thermal efficiency of the equipment and decrease the separation efficiency of the distillation towers. In addition, operating modifications to reduce the rate of fouling can result in reduced production capacity. The excessive build-up of such deposits can cause plugging in tower plates, transfer tubes, and process lines, which could result in unplanned shutdowns. These deposits are generally thought to result from free radical polymerization induced thermally, by contaminating oxygen or by metal ions. Similar problems are also encountered in olefin recovery operations not connected with thermal cracking, for example, in styrene recovery.

Such fouling can be controlled according to the present invention, by the judicious use of an appropriate stable free radical or a suitable precursor that under the process conditions yields the active stable free radical in situ. The fouling is controlled by the action of the stable free radicals in terminating radical polymerization chain reactions in the processing equipment.

2. Related Art

The use of stable nitroxides and other stable free radicals and precursors thereto are well documented in the patent and open literature as stabilizers for olefinic organic compounds. The prior art teaches that these stable free radicals are useful for the prevention of premature radically induced polymerization of the olefinic monomer during storage and as antioxidants. Typical of this art is U.S. Pat. No. 3,747,988 on the stabilization of acrylonitrile; U.S. Pat. No. 3,733,326 disclosing stabilization of vinyl monomers by free radical precursors; U.S. Pat. No. 3,488,338 on the stabilization of chloroprene; UK Pat. Spec. No. 1,127,127 relating to the stabilization of acrylic acid; UK Pat. Spec. No. 1,218,456 relating to the stabilization of butadiene and the following publications "Inhibition of Radical Polymerization by Nitroxide Mono and Biradicals", L. V. Ruban, et al, Vysokomol. soyed. 8: No. 9, p. 1642–1646, 1966; "Iminoxy Radicals as Inhibitors of w-Polymerization of Chloroprene", M. B. Nieman, et al, Vysolomol. soyed, 8: No. 7, p. 1237–1239, 1966; "Inhibition of Polymerization of Styrene by a Stable Radical with 4,4'diethoxy-diphenyl Nitric Oxide", M. D. Goldfein, et al, Vysokomol. soyed. A 16: No. 3, p. 672–676, 1974; "Inhibition of Polymerization of Vinyl Monomers by Nitroxide and Iminoxyl Radicals", A. V. Trubnikov, et al., Vysokomol. soyed. A20: No. 11, p. 2448–2454, 1978.

This art, without exception discloses the use of stable free radicals in excess of 1 ppm and generally well in excess of 10 ppm. Although there is a body of art relating to stable free radicals, these materials are very expensive and usually available or produced only in very limited quantities for research. Hence, the art has consistently taught that which it considered to be the smallest effective amount of stable free radical for stabilization as at least 1 ppm (actually the major portion of the art teaches over 10 times this amount). It has now been surprisingly found that fouling caused by polymerization of olefinic organic compounds can be effectively controlled with substantially less than the 1 ppm of stable free radical taught by the art as the lowest level. Although the stable nitroxide free radical compounds are currently, principally of academic interest there is an abundance of art on their preparation, for example, the following U.S. Pat. Nos., 3,494,930; 3,966,711; 3,704,233; 3,334,103; 3,253,015; 3,372,182; 3,502,692; 3,422,144; 3,163,677 and 3,873,564.

It is an advantage of the present invention that fouling in processing equipment for hydrocarbon streams containing olefinic organic compounds, may be controlled by the present invention. It is a feature of the present invention that stable free radicals, which have been laboratory curiosities until now because of their high cost, can now be beneficially employed commercially for stabilization. These and other advantages and features will become apparent from the following description.

SUMMARY OF THE INVENTION

Generally the present invention relates to the discovery that polymerization of unsaturated organic compounds (olefinic or acetylenic unsaturation) contained in organic feed streams can be controlled and inhibited during processing of the streams by incorporating from about 20 up to about 900 ppb, of a stable free radical into the stream, based on the total stream being processed. Briefly, the present invention is a method for inhibiting polymerization of unsaturated compounds in organic feed streams during processing of said feed streams comprising having present from about 50 to less than 1000 ppb, preferably 50 to 900 ppb and more preferably less than 700 ppb by weight of a stable free radical, based on the total weight of said feed stream, thereby controlling fouling of processing equipment.

The feed streams may be hydrocarbons or unsaturated compounds and may contain other substituents in addition to hydrogen and carbon. Similarly the entire feed stream may be comprised of substituted hydrocarbons. The unsaturated compounds may comprise from 1 to 100% of the feed stream.

The processing may include distillation, extraction, heating, vaporizing and hydrotreating of the feed stream, wherein the unsaturated compound is removed, concentrated or reacted, as in hydrotreating, or some other component of the feed stream is removed, concentrated or reacted. The amount of stable free radical used in the process is quite small, hence product streams, e.g., olefins, produced according to the present method can be utilized for polymerization by the addition of conventional amounts of polymerization catalyst under polymerization conditions, which will overcome the inhibiting effect of any stable free radical remaining in the product. In distillation the stable free radical may be selected to be higher boiling than the overhead, hence it will remain bottoms. Thus, for example, in ethylene recovery there will be no stable free radical in the ethylene overhead product to interfere with subsequent polymerization. The present method excludes any process carried out for the purpose of polymerizing the unsaturated compounds, particularly in the presence of effective amounts of polymerization catalyst. In a particular application it has been found that the spontaneous and unexplained formation of "popcorn polymer" in distillation equipment in the vapor portion of the equipment used to separate and recover some olefins, e.g., butadiene and styrene overhead, is inhibited according to the present invention.

The products resulting from the present method of processing may also be stabilized from unsaturated hydrocarbon polymerization provided the appropriate amount of the stable free radical, as recited above for the feed stream processing, is present in the product.

The term "stable free radical" as used herein shall mean a free radical that can be prepared by conventional chemical methods and will exist long enough to be used in a subsequent chemical reaction or examined in a static system by normal methods of spectroscopy. Generally the stable free radicals of the present invention have a half life of at least one (1) year. The term "half life" as used herein means that period of time at the end of which one-half of the radicals, existing at the beginning of said time period are still in existence. The term "stable free radical" shall also be understood to include the precursor to a stable free radical from which the stable free radical may be produced in situ.

DETAILED DESCRIPTION OF THE PRESENT INVENTION AND PREFERRED EMBODIMENTS

Figure 1:
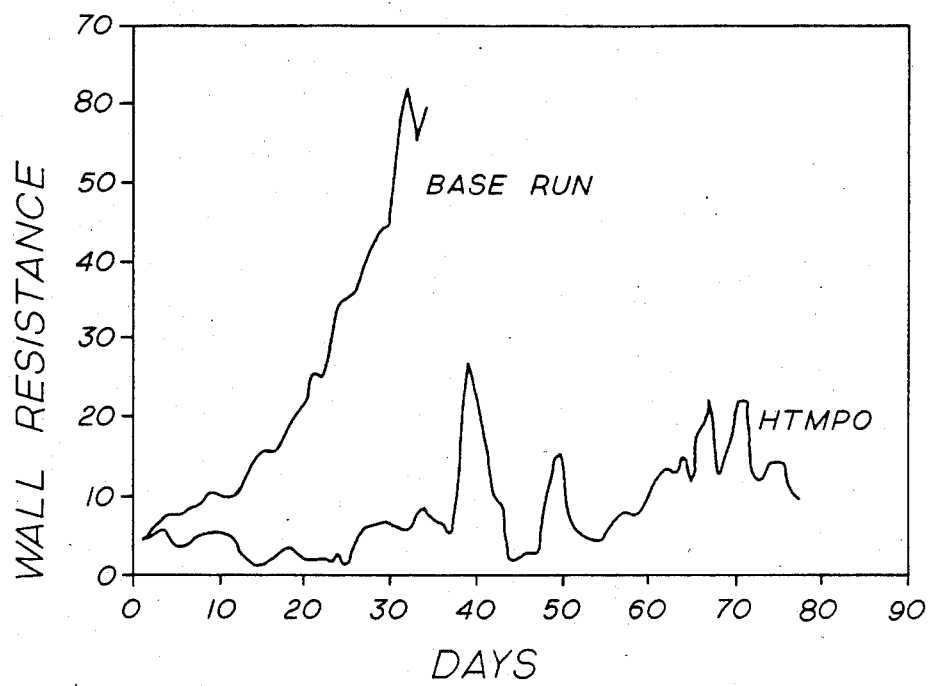
FIG. 1 is a plot showing the results from a process carried out according to the present invention and from the same process carried out in accordance with prior practice. The scale of the wall resistance is increased by a factor of $10^4$ for the drawing.

Any stable free radical (or precursor thereof under conditions which produce the stable free radical in situ) as defined may be used in the present invention. The stable free radicals suitable for use in this invention may be selected from, but are not limited to, the following groups of chemicals: nitroxides (e.g., di-tert butylnitroxide), hindered phenoxys (e.g., galvinoxyl), hydrazyls (e.g., diphenylpicrylhydrazyl), and stabilized hydrocarbon radicals (e.g., triphenylmethyl), as well as polyradicals, preferably biradicals of these types. In addition, certain precursors that produce stable free radicals in situ may be selected from the following groups: nitrones, nitrosos, thioketones, benzoquinones, and hydroxylamines.

These stable free radicals exist over a wide range of temperatures up to about 500° F. A limiting factor in their use is the temperature of the processing wherein they are employed. Specifically the present method applies to processing carried on at temperatures at which said stable free radical exists. Generally such processing is conducted at less than 500° F., e.g., 0° to 500° C. Pressure has not been seen to be significant to the present method, hence, atmospheric, sub or superatmospheric conditions may be employed. A preferred stable free radical for use in this invention is a nitroxide having the formula:

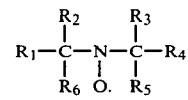

wherein $R_1$, $R_2$, $R_3$ and $R_4$ are alkyl groups or heteroatom substituted alkyl groups and no hydrogen is bound to the remaining valences on the carbon atoms bound to the nitrogen.

The alkyl (or heteroatom substituted) groups $R_1$–$R_4$ may be the same or different, and preferably contain 1 to 15 carbon atoms. Preferably $R_1$–$R_4$ are methyl, ethyl, or propyl groups. In addition to hydrogen the heteroatom substituents may include, halogen, oxygen, sulfur, nitrogen and the like.

The remaining valences ($R_5$ and $R_6$) in the formula above may be satisfied by any atom or group except hydrogen which can bond covalently to carbon, although some groups may reduce the stabilizing power of the nitroxide structure and are undesirable. Preferably $R_5$ and $R_6$ are halogen, cyano, —COOR wherein R is alkyl or aryl, —CONH$_2$, —S—C$_6$H$_5$, —S—COCH$_3$, —OCOC$_2$H$_5$, carbonyl, alkenyl where the double bond is not conjugated with the nitroxide moiety or alkyl of 1 to 15 carbon atoms, $R_5$ and $R_6$ may also form a ring of 4 or 5 carbon atoms and up to two heteroatoms, such as O, N or S by $R_5$ and $R_6$ together. Examples of suitable compounds having the structure above and in which $R_5$ and $R_6$ form part of the ring are pyrrolidin-1-oxys, piperidinyl-1-oxys, the morpholines and pierazines. Particular examples wherein the $R_5$ and $R_6$ above form part of a ring are 4-hydroxy-2,2,6,6-tetramethyl-piperindino-1-oxy, 2,2,6,6-tetramethyl-piperidino-1-oxy, 4-oxo-2,2,6,6-tetramethyl-piperidino-1-oxy and pyrrolin-1-oxyl. Suitable $R_5$ and $R_6$ groups are methyl, ethyl, and propyl groups. A specific example of a suitable compound where $R_1$–$R_6$ are alkyl groups is di-tert-butylnitroxide. The preferred carbonyl containing nitroxides are those wherein the $R_5$ and $R_6$ form a ring structure with the nitrogen, preferably a six number ring, for example, 4-oxo-2,2,6,6-tetramethylpiperidino-1-oxy.

The feed streams are organic, preferably hydrocarbons containing hydrocarbon olefinic and/or acetylenic compounds. The unsaturated compounds may be pure hydrocarbons or organic unsaturated compounds or mixtures thereof.

The processing to which the present invention is directed includes distillation, extraction, extractive distillation, countercurrent extraction, hydrotreating, hydrofining, thermal treatments and the like, and the preheating prior to such processing. Those processes which are intended to produce polymer by free radical initiation, coordination type catalyst, or otherwise are excluded; however, the presence of the present stable free radicals in feeds used for polymerizations as a result of prior processing according to the present invention is not precluded, since the catalytic concentrations of polymerization catalyst readily overwhelm the parts per billion of stable free radical residual from the present invention.

The olefinic compounds include hydrocarbon monomers generally having two to 20 carbon atoms such as ethylene, propylene, butene-1, isobutene, pentene, hexene, octene, dodecene, butadiene, isoprene, hexadiene and the like; vinyl monomers such as vinyl chloride, vinyl acetate, vinylidene chloride, ethyl vinyl ketone, chloroprene, styrene, divinylbenzene, vinyl pyridiene, chlorostyrenes, esters of acrylic acid and methacrylic acid, acrylamide, acrylonitrile, methacrylonitrile, acrolein, methacrolein and the like. Acetylenic compounds include, for example vinyl acetylene, methyl acetylene and the like. The unsaturated compounds may also include higher molecular weight compounds found in crude oil and crude oil distillates and residua which are normally identified by their solubility characteristics, such as asphaltenes and maltenes.

The processing carried out according to the present invention results in a wide variety of liquid (under the appropriate conditions of pressure) compositions containing the stable free radical. Some of these compositions may contain olefinic materials for use in polymerizations or otherwise or for other end uses or processing.

There may be present in the present method in addition to the stable free radical as described, other additives such as antioxidants, anti-foaming agents, color stabilizers and the like.

A preferred mode of operation for the present invention is the fractionation of an organic feed stream to recover olefinic compound contained therein, e.g., low molecular weight olefinic hydrocarbons, thereby inhibiting polymerization and controlling fouling in the distillation towers, reboilers and associated equipment, a particular example of such a separation being the removal of ethylene from a low boiling hydrocarbon cut, e.g., a $C_7$ cut. Past experience with the operation of a deethanizer unit has shown that polymer build up resulting in fouling of the distillation tower walls and plugging of reboiler tubes required a shut down of the reboiler about every thirty days for removal of the polymer. The primary detriment from the fouling is the reduction in the heat transfer in the reboiler of the tower. In order to avoid fouling, milder conditions are frequently used, requiring recycle of the distillate products, lower compressor efficiency and higher refrigeration costs. In order to maintain a given level of operation at a given pressure the heat input to the tower must be increased as the polymer builds up. The same processing carried out according to the present method results in low levels of fouling. This is shown by FIG. 1 where a deethanizer was operated without a stable free radical and had an increase in wall resistance to the point that it was necessary to shut down for cleaning at around 36 days (Base Run). Wall resistance is the resistance of a wall to the flow of thermal energy from one side to the other. In this instance, wall resistance refers to the transfer of heat across the walls of tubes in a reboiler. In this regard it is qualitatively the inverse of the more conventionally used heat transfer coefficient. The wall resistance values used in FIG. 1 are derived from heat transfer coefficient values and appropriate corrections for steam rates, process rates, condensate levels, and other similar parameters affecting the operation of the trial unit expressed as Hour, feet squared, degrees fahrenheit per BTU (hr $ft^2$ °F./BTU).

Wall resistance can be used as an indicator of fouling because of the fact that as fouling material is deposited on the heat transfer surface it forms an additional layer of resistance that must be overcome. Because the wall resistance is calculated from the temperature difference of the fluids on each side of the wall, this layer of fouling causes an increase in the calculated wall resistance. Thus an increase in the wall resistance is indicative of an increase in fouling.

Brief excursions, such as those seen in FIG. 1, may arise from sudden changes in process conditions that are not accounted in the wall resistance calculations. Fouling is indicated by the long-term trend of the wall resistance.

The same equipment and process carried out in the presence of less than 500 ppb 4-hydroxy-2,2,6,6-tetramethylpiperindinyloxy (HTMPO) based on bottoms production rate showed almost no polymer build up as evidenced by the low wall resistance during the same period and has continued to operate without fouling for over 100 days.

To further demonstrate the effectiveness of the present invention two stable free radicals were tested against several commercial anti-fouling additives on an apparatus designed to simulate fouling in a dynamic manner. This test is designed to detect the formation of insoluble polymer by passing the test fluid through an orifice. The fouling of a particular fluid is detected by recording the change in the pressure across an appropriately sized orifice through which the test fluid is passed. The deposition of fouling material on the surface of the orifice restricts the flow path resulting in an increase in the pressure drop over the length of the orifice.

The analysis of the effects of additives is accomplished by comparing the times required for the pressure difference across the orifice to reach a predetermined value for a fluid containing the additive and the fluid alone. The variation in the characteristics of the fluids and the configuration of the analyzer compared to that of a full-scale plant precludes an extrapolation of the results from laboratory to plant. However, the results are useful in identifying additives that inhibit fouling of the test fluids and in ranking the effectiveness of several additives in inhibiting fouling.

The formation of polymer is detected by observing the change in the pressure drop across the restriction. Run length is defined as the time required for the pressure to increase by a predetermined amount. Table 1 shows the results of tests on a number of compounds and formulations which are active in inhibiting the formation of the polymeric fouling material.

TABLE 1

| ADDITIVE | RUN LENGTH (MINUTES) |
| --- | --- |
| Blank Feed (50% butadiene) | 5-6 |
| Commercial Additives (10,000 ppb - active concentration) | |
| 2,6-Di-tert-butyl-4-methylphenol (BHT) | 7.3 |
| 4-Methoxyphenol (MEHQ) | 7.4 |
| Nonylphenol-formaldehyde resin (50% active) | 9.1 |
| Nonylphenol-formaldehyde resin-Trisnonylphenylphosphite | 11.5 |
| Formulation 7* | 8.3 |
| Formulation 10* | 9.9 |
| Invention Additives 100 ppb | |
| 4-Hydroxy-2,2,6,6-tetramethyl-piperidinyloxy (HTMPO) | 8.6 |
| Di-tert-butylnitroxide | 13.6 |

*Proprietary blend of dispersant, antioxidant and metal chelant

As can be seen from the length of runs in TABLE 1 the stable free radical will obtain substantially the same result as 100 times as much of the commercial additives.

Table 2 summarizes the results of treating a similar feed with HTPMO.

TABLE 2

| ADDITIVE (CONCENTRATION) | RUN LENGTH (MINUTES) |
|---|---|
| Blank feed (50% butadiene) | 13.1 |
| Blank feed (50% butadiene) | 13.8 |
| HTMPO (100 ppb) | 72 |
| HTMPO (2000 ppb) | 92 |

This example demonstrates that a twenty fold increase in stable free radical produces only a small incremental increase in fouling inhibition.

The invention claimed is:

1. In a process wherein an organic feed stream containing one or more unsaturated oelfinic hydrocarbons is separated into an overhead stream of an olefinic compound selected from ethylene, propylene, butenes, butadiene and mixtures thereof, and a bottoms liquid containing other unsaturated olefinic hydrocarbon liquids including one or more $C_2$ to $C_7$ hydrocarbons, the improvement wherein an effective amount of a stable free radical is introduced into the feed stream to inhibit fouling by the bottoms liquid, said stable free radical being a nitroxide having a boiling point above the separated olefinic compound whereby said stable free radical remains in the bottoms liquid, the concentration of said stable free radical in the feed stream being less than 700 parts per billion.

2. The method according to claim 1 wherein said stable free radical is a nitroxide having the formula:

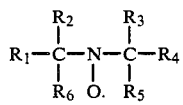

wherein each of $R_1$, $R_2$ and $R_3$ and $R_4$ is an alkyl group or heteroatom substituted alkyl group having 1 to 15 carbon atoms, $R_5$ and $R_6$ (a) each being an alkyl group having 1 to 15 carbon atoms, or a substituted alkyl group having 1 to 15 carbon atoms wherein the substituent is halogen, cyano, —$CONH_2$, —$SC_6H_5$, —S—$COCH_3$, —$OCOCH_3$, —$OCOC_2H_5$, carbonyl, alkenyl wherein the double bond is not conjugated with the nitroxide moiety, or —COOR wherein R of the —COOR group is alkyl or aryl, or (b) together forming part of a ring that contains 4 or 5 carbon atoms and up to two heteratoms of O, N or S.

3. The method according to claim 2 wherein the $R_1$, $R_2$, $R_3$ and $R_4$ groups are each methyl, ethyl or propyl groups.

4. The method according to claim 3 wherein $R_5$ and $R_6$ are each methyl, ethyl or propyl groups.

5. The method according to claim 1 wherein the nitroxide is di-tert-butyl-nitroxide.

6. The method accordinq to claim 3 wherein the nitroxide is a piperdino-1-oxyl, a pyrrolidino-1-oxyl or a pyrrolin-1-oxyl.

7. The method according to claim 6 wherein the nitroxide is 4-hydroxy-2,2,6,6-tetramethylpiperidino-1-oxy.

8. The method according to claim 6 wherein the nitroxide is 4-oxo-2,2,6,6-tetramethylpiperidino-1-oxy.

9. The method according to claim 6 wherein the nitroxide is 2,2,6,6-tetramethylpiperidino-1-oxy.

10. The method according to claim 3 wherein said nitroxide is 4-hydroxy-2,2,6,6-tetramethylpiperidino-1-oxy.

11. The method according to claim 3 wherein the nitroxide is di-tert-butylnitroxide.

12. The method according to claim 1 wherein said stable free radical is produced in situ from a precursor.

13. The method according to claim 3 wherein said stable free radical is produced in situ from a precursor.

14. The method according to claim 2 wherein the ring structure formed by $R_5$ and $R_6$ contains a carbonyl.

15. The method as defined in claim 2 wherein the concentration of free radical in the bottoms liquid is less than 500 parts per billion.

16. The method as defined in claim 1 wherein the concentration of free radical in the bottoms liquid is less than 500 parts per billion.

17. The method as defined in claim 1 wherein the stable free radical is HTMPO and is present in the bottoms liquid at a concentration of less than 500 parts per billion.

18. The method of claim 2 wherein the nitroxide is present in the feed stream at a concentration of between about 20 to about 100 parts per billion.

19. The method as defined in claim 10 wherein the concentration of said nitroxide in the bottoms liquid is less than 500 parts per billion.

20. The process as defined in claim 1 wherein the hydrocarbon separated into an overhead stream is ethylene.

* * * * *